United States Patent [19]

Goldenberg

[11] Patent Number: 4,830,460
[45] Date of Patent: May 16, 1989

[54] GUIDANCE SYSTEM AND METHOD FOR DELIVERY SYSTEM FOR HIGH-ENERGY PULSED ULTRAVIOLET LASER LIGHT

[75] Inventor: Tsvi Goldenberg, Irvine, Calif.

[73] Assignee: Advanced Interventional Systems, Inc., Costa Mesa, Calif.

[21] Appl. No.: 51,382

[22] Filed: May 19, 1987

[51] Int. Cl.⁴ .................. G02B 23/26; A61N 5/06
[52] U.S. Cl. ................................. 350/96.26; 128/6; 350/96.10; 350/96.15
[58] Field of Search ............... 350/96.26, 96.10, 96.34, 350/96.15; 128/6

[56] References Cited

U.S. PATENT DOCUMENTS

| | | | |
|---|---|---|---|
| 4,009,382 | 2/1977 | Nath | 350/96 R |
| 4,011,403 | 3/1977 | Epstein et al. | 350/96.10 X |
| 4,170,997 | 10/1979 | Pinnow et al. | 350/96.26 X |
| 4,173,393 | 11/1979 | Maurer | 350/96.34 |
| 4,207,874 | 6/1980 | Choy | 128/6 |
| 4,270,845 | 6/1981 | Takizawa et al. | 350/299 |
| 4,272,156 | 6/1981 | Ishibashi et al. | 350/96.26 |
| 4,305,640 | 12/1981 | Cullis et al. | 350/96.10 |
| 4,398,790 | 8/1983 | Righini et al. | 350/96.18 |
| 4,418,688 | 12/1983 | Loeb | 128/6 |
| 4,490,020 | 12/1984 | Sakaguchi et al. | 350/96.18 |
| 4,521,070 | 6/1985 | Sottini et al. | 350/96.26 |
| 4,565,197 | 1/1986 | Daly | 350/96.29 |
| 4,569,335 | 2/1986 | Tsuno | 350/96.26 |
| 4,641,912 | 2/1987 | Goldenberg | 350/96.26 X |
| 4,681,104 | 7/1987 | Edelman | 128/303.1 |
| 4,686,963 | 8/1987 | Cohen et al. | 350/96.26 X |
| 4,686,979 | 8/1987 | Gruen et al. | 128/303.1 |
| 4,696,544 | 9/1987 | Costella | 350/96.26 |

FOREIGN PATENT DOCUMENTS 59-111125 6/1984 Japan .
1042281 9/1966 United Kingdom .

OTHER PUBLICATIONS

Lasers in Surgery and Medicine, vol. 4, issued 25 Jul. 1984, "Far-Ultraviolet Laser Ablation of Atherosclerotic Lesions".

Primary Examiner—John D. Lee
Assistant Examiner—Phan T. Heartney
Attorney, Agent, or Firm—Burns, Doane, Swecker & Mathis

[57] ABSTRACT

A fiber-optic instrument, used for ablating lesions in blood vessels, is mounted to and guided by a sleeve having two lumens extending therethrough and parallel to each other. The instrument fits within one lumen and a guidewire, previously inserted in a blood vessel, extends through the other lumen. The sleeve and instrument are advanced along the guidewire within the blood vessel. An inflatable balloon may be provided at the distal end of a fiber optic instrument for retaining saline in order to displace opaque blood that would otherwise surround the distal end of the instrument.

22 Claims, 9 Drawing Sheets

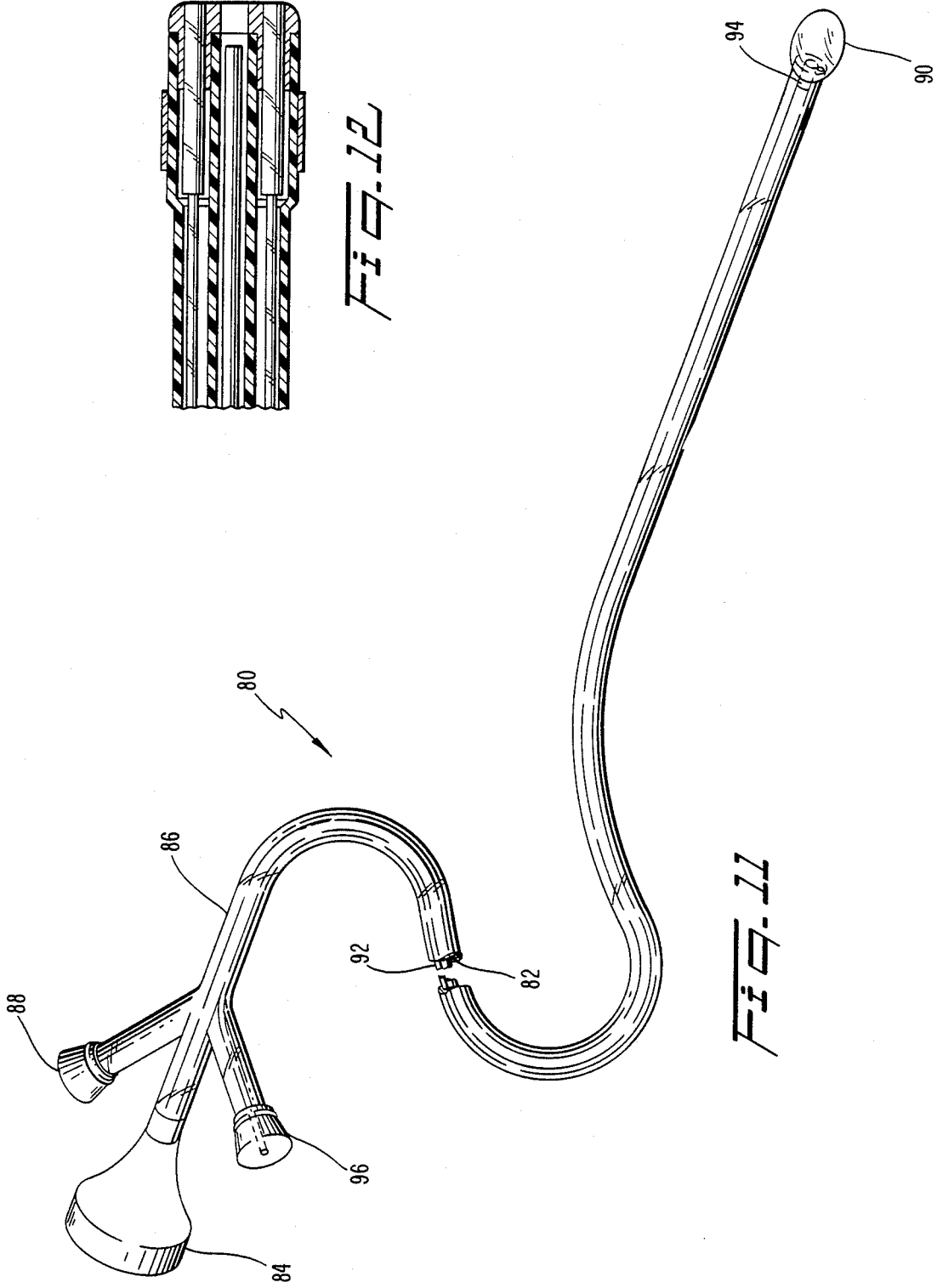

GUIDANCE SYSTEM AND METHOD FOR DELIVERY SYSTEM FOR HIGH-ENERGY PULSED ULTRAVIOLET LASER LIGHT

CROSS-REFERENCE TO RELATED APPLICATIONS

This is a continuation-in-part of application Ser. No. 860,241 filed May 6, 1986, which is a continuation-in-part of application Ser. No. 779,844 filed Sept. 25, 1985 (now U.S. Pat. No. 4,732,448, which is itself a continuation-in-part of application Ser. No. 679,538 filed Dec. 7, 1984 (now U.S. Pat. No. 4,641,912), the disclosures of which are herein incorporated by reference thereto.

BACKGROUND OF THE INVENTION

The present invention is directed to a system for delivering high energy laser light by means by an optical waveguide, and in one particular application is concerned with laser angioplasty and a means for guiding such a system.

The use of laser energy to ablate atherosclerotic plaque that forms an obstruction in a blood vessel is presently being investigated as a viable alternative to coronary bypass surgery. This procedure, known as angioplasty, essentially involves insertion of a fiberoptic waveguide into the vessel, and conduction of laser energy through the waveguide to direct it at the plaque once the distal end of the waveguide is positioned adjacent the obstruction. To enable the physician to ascertain the location of the waveguide as it is being moved through the vessel, additional waveguides for providing a source of illuminating light and for conducting the image from inside the vessel back to the physician are fed together with the laser waveguide. Typically, the three waveguides are encapsulated within a catheter.

Most of the experimentation and testing that has been done in this area has utilized continuous wave laser energy, such as that produced by Argon Ion, Nd:YAG or Carbon Dioxide lasers. The light produced by this type of laser is at a relatively low energy level. Ablation of the obstruction is achieved with these types of lasers by heating the plaque with constant laser power over a period of time until the temperature is great enough to destroy it.

While the use of continuous wave laser energy has been found to be sufficient to ablate an obstruction, it is not without its drawbacks. Most significantly, the destruction o the lesion is uncontrolled and is accompanied by thermal injury to the vessel walls immediately adjacent the obstruction. In an effort to avoid such thermal injury and to provide better control of the tissue removal, the use of a different, higher level form of laser energy having a wavelength in the ultra-violet range (40–400 nanometers) has been suggested. See, for example, International Patent Application PCT/US84/02000, published June 20, 1985. One example of a laser for producing this higher level energy is known as the Excimer laser, which employs a laser medium such as argon-chloride having a wavelength of 193 nanometers, krypton-chloride (222 nm), krypton-fluoride (248 nm), xenon-chloride (308 nm) or xenon-fluorine (351 nm). The light produced by this type of laser appears in short bursts or pulses that typically last in the range of ten to hundreds of nanoseconds and have a high peak energy level, for example as much as 200 mJ. Although the destruction mechanism involving this form of energy is not completely understood, it has been observed that each single pulse of the Excimer laser produces an incision which destroys the target tissue without accompanying thermal injury to the surrounding area. This result has been theorized to be due to either or both of two phenomena. The delivery of the short duration, high energy pulses may vaporize the material so rapidly that heat transfer to the non-irradiated adjacent tissue is minimal. Alternatively, or in addition, ultraviolet photons absorbed in the organic material might disrupt molecular bonds to remove tissue by photochemical rather than thermal mechanisms.

While the high peak energy provided by Excimer and other pulsed lasers has been shown to provide improved results with regard to the ablation of atherosclerotic plaque, this characteristic of the energy also presents a serious practical problem. Typically, to couple a large-diameter laser beam into a smaller diameter fiber, the fiber input end is ground and polished to an optical grade flat surface. Residual impurities from the polishing compound and small scratches on the surface absorb the laser energy. These small imperfections result in localized expansion at the surface of the fiber when the laser energy is absorbed. The high-energy Excimer laser pulses contribute to high shear stresses which destroy the integrity of the fiber surface. Continued application of the laser energy causes a deep crater to be formed inside the fiber. Thus, it is not possible to deliver a laser pulse having sufficient energy to ablate tissue in vivo using a conventional system designed for continuous wave laser energy.

This problem associated with the delivery of high energy laser pulses is particularly exacerbated in the field of coronary angioplasty because of the small diameter optical fibers that must be used. For example, a coronary artery typically has an internal diameter of two millimeters or less. Accordingly, the total external diameter of the angioplasty system must be below two millimeters. If this system is composed of three separate optical fibers arranged adjacent one another, it will be appreciated that each individual fiber must be quite small in cross-sectional area.

A critical parameter with regard to the destruction of an optical fiber is the density of the energy that is presented to the end of the fiber. In order to successfully deliver the laser energy, the energy density must be maintained below the destruction threshold of the fiber. Thus, it will be appreciated that fibers having a small cross-sectional area, such as those used in angioplasty, can conduct only a limited amount of energy if the density level is maintained below the threshold value. This limited amount of energy may not be sufficient to efficiently ablate the obstructing tissue or plaque without thermal damage.

A further problem with the use of a fiberoptic waveguide to direct laser energy for purposes of ablating atherosclerotic plaque is that of perforation of the blood vessel. Such perforations can be caused by the waveguide itself contacting and perforating the vessel. Such perforations can also be caused by the laser beam, particularly if the waveguide is not aligned properly within the blood vessel. The perforation problems are related to the intrinsic stiffness of the glass fibers of the waveguide and poor control of laser energy, regardless of laser source or wavelength.

Also related to the stiffness of the glass fibers is the ability to control the position of the fibers radially within the blood vessels. The conventional systems employing fiberoptic waveguides within a blood vessel do not provide means for controlling radial movement within the blood vessel.

Guiding a fiberoptic waveguide (angioscope) within a blood vessel is also made difficult by the opaque nature of blood, which severely limits visibility in front of the scope. In some cases saline is pumped into the vessel in front of the scope, temporarily replacing the opaque blood with a clear fluid. However, the saline must be used sparingly to minimize the risk to the patient, particularly in cases of coronary angioscopy.

OBJECTS AND BRIEF STATEMENT OF THE INVENTION

Accordingly, it is a general object of the invention to provide a novel system for delivering high energy pulsed laser light using an optical waveguide.

It is a more specific object of the invention to provide such a delivery system that is particularly well suited to deliver ultraviolet laser energy in vivo for the ablation of atherosclerotic plaque. In this regard, it is a particular object of the present invention to provide highly efficient waveguide for use in such a delivery system.

It is yet another object of the present invention to provide such a delivery system that is adapted to minimize the likelihood of perforating or otherwise damaging a blood vessel in which the system is being used.

It is a further object of the present invention to provide such a system that includes a guide for facilitating the maneuvering of the optical waveguides through the blood vessel in which the system is being used.

It is another object of the present invention to provide a device for controlling the radial movement of the optical waveguide within the blood vessel in which the system is being used.

It is still another object of the present invention to provide a device for improving the visibility of an angioscope within a blood vessel while limiting the quantity of saline that is introduced into the circulatory system.

Briefly, one aspect of a delivery system embodying the present invention relates to a guidance system that facilitates guiding an optical fiber system through a blood vessel. In a preferred form, the guidance system comprises a guidewire that is inserted into the blood vessel prior to the insertion of the optical fiber, and a sleeve having a rounded distal end and two lumens therein. The distal end of the optical fiber is bonded within one of the sleeve lumens. The wire, which has already been inserted into the blood vessel, is then threaded through the second sleeve lumen. The sleeve and optical fiber are then advanced along the wire until the optical fiber is positioned adjacent a lesion to be ablated by a laser system incorporated with the optical fiber system.

Radial control of the optical fiber within the blood vessel may be had by locating the fiber lumen eccentrically within the sleeve. Thus by rotating the optical fiber, the optical fiber will be moved to different radial positions within the blood vessel.

Furthermore, visibility of an angioscope is enhanced by providing an elastic inflatable balloon around a lens output at the angioscope distal end. The balloon is transparent and is inflated with clear saline. The inflated balloon displaces the opaque blood and provides a field of view before the angioscope. The balloon arrangement can also be used with a laser system incorporated with the angioscope.

Further features of the present invention and preferred modes for implementing them will become apparent from the following detailed description of preferred embodiments of the invention illustrated in the accompanying drawings.

BRIEF DESCRIPTION OF THE DRAWINGS

FIG. 11 is a perspective view of an endoscope in a catheter with an inflatable balloon at the distal end; and FIG. 12 is a cross-sectional view of an alternative embodiment including means for extending the diameter of a beam of laser energy emerging from the distal end thereof.

DESCRIPTION OF THE ILLUSTRATED EMBODIMENTS

Figure 1:
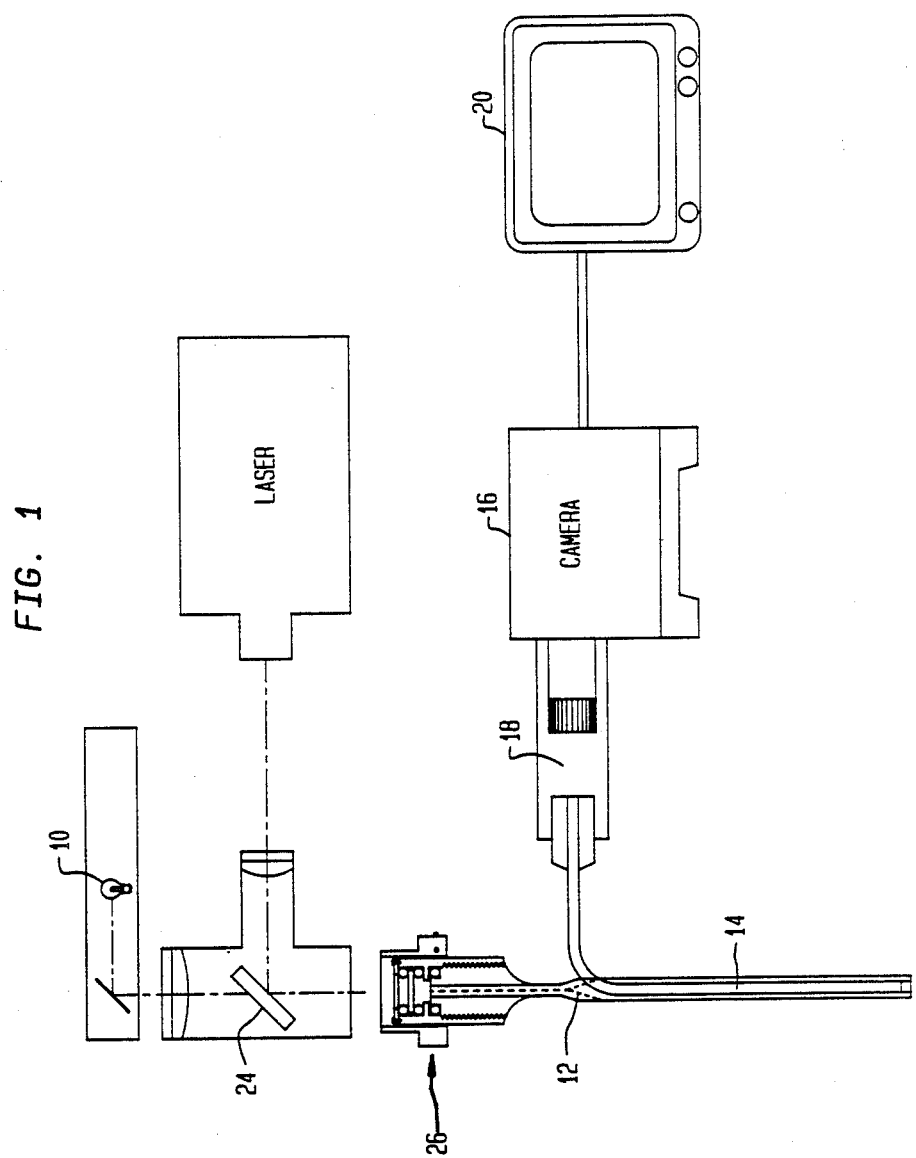
FIG. 1 is a schematic diagram of a laser and image delivery system that can be used for angioplasty.

In the following specification, a laser delivery system is described with particular reference to the use of Excimer laser energy in an angioplasty system, in order to facilitate an understanding of the invention and its uses. Referring to FIG. 1, an angioplasty arrangement that can employ the delivery system of the present invention is shown in schematic form. The angioplasty system must be capable of performing three functions within the blood vessel. The first two of these relate to the illumination and imaging of the interior of the vessel to enable a physician to successfully propagate the distal end of the system through the vessel to the location of the obstruction. Accordingly, the output from a source of visible light, such as a Halogen or Xenon lamp 10, is directed to the proximal end of an optical fiber 12. The distal end of this fiber is housed within a catheter (not shown) to enable it to be fed through a blood vessel. A second optical fiber 14 located adjacent the fiber 12 within the catheter receives the image from the illuminated interior of the blood vessel and transmits it to a video camera 16 by means of a video coupler 18 connected between the output end of the fiber 14 and the camera. The image presented to the camera 16 by the fiber 14 is converted into a video signal and fed to a suitable monitor 20 for viewing by the physician as the catheter is being positioned inside the blood vessel. Alternatively, the video coupler, camera and monitor can be replaced by an eyepiece that is attached to the proximal end of the fiber 14.

Once the distal ends of the fibers 12 and 14 have been appropriately positioned adjacent the obstruction, a high energy pulsed ultraviolet laser, such as an Excimer laser, is activated to ablate the obstruction. In a preferred implementation of the invention, the laser light is conducted along the same optical fiber 12 as the visible light. To accomplish such a result, the output beam of the laser is directed at a beam splitter 24 which also transmits the visible light from the source 10. These two forms of light energy are propagated along the same path and presented to the input end of the optical fiber 12 by means of an energy coupler 26.

Figure 2:
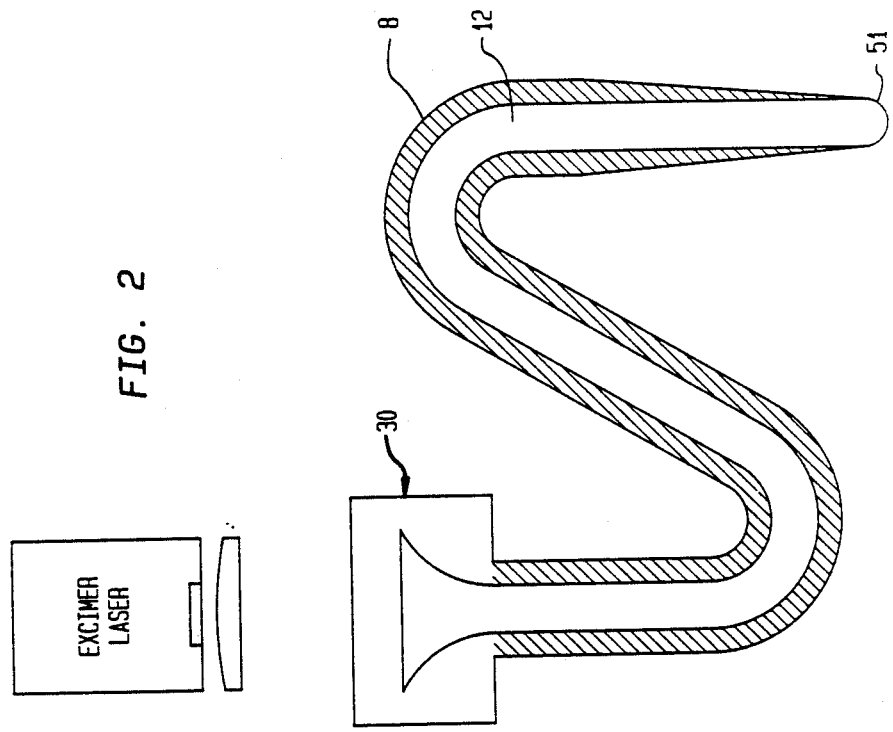
FIG. 2 is a cross-sectional side view of a delivery system for high energy Excimer laser light utilizing a funnel-shaped energy coupler.

Referring now to FIG. 2, one embodiment of the delivery system for high energy pulsed laser light is illustrated in greater detail. The delivery system essentially comprises three basic elements. The first of these is the optical fiber 12. A fiber that is particularly suitable for use in the delivery of high energy pulsed ultraviolet laser light is a multi-mode fiber which has a relatively large core, or active area, relative to the area of its cladding, i.e., the outer skin of the fiber. The core is made of substantially pure synthetic fused silica, i.e. amorphous silicon dioxide. This material preferably has a metallic impurity content of no more than 30 parts per million, to provide better conduction of the transmitted laser energy than that which is obtainable with natural fused quartz. The term "metallic impurity" includes both metals per se and oxides thereof.

Even with such a low level of metallic impurity, defects in the silica fiber can serve as linear and non-linear absorption sites for the photons. These defects can vary from oxygen vacancy to unbonded silicon atoms found in any silica glass. They can result in lowered transmittance of ultraviolet radiation. Increasing the intensity (or energy) of the laser light that is introduced into one end of a fiber exhibiting such defects will not necessarily result in proportionally increased output at the other end. Rather, the increased intensity level can reduce the threshold level at which bulk damage occurs to the silica glass, and thereby destroys the delivery system.

In accordance with one aspect of the present invention, the transmittance of high energy UV laser light in a fiber made of synthetic silica is enhanced by lightly doping the silica with a material which functions to repair some of the inherent structural defects of the silica. The silica is preferably doped with an $OH^-$ radical, to thereby form so-called "wet" silica. It is believed that defects in silica that affect UV light transmission comprise oxygen hole centers and unbonded silica atoms. It is theorized that the doping of the silica with the $OH^-$ radical functions to repair these defects by eliminating the oxygen holes or vacancies in one case and by bonding to the silicon to form the $SiO_2$ double bond. It has been reported that pure silica having only about 5 parts per million (ppM) of an OH radical has an absorption coefficient which is 2-3 times greater than silica having about 1200 ppM of the radical. See J. H. Stathes et al, *Physical Review B.*, Vol. 29, 12, 1984, pp. 70–79. Other investigations have reported that an optical absorption band appears in silica fibers having a low $OH^-$ content as a result of the fiber drawing process. See Kaiser et al, *J. Opt. Soc. Am.* 63, 1973, p. 1141 and *J. Opt. Soc. Am.* 63, 1974, p. 1765. Apparently, an increase in the $OH^-$ content o silica reduces both types of absorption sites described above, and in accordance with the present invention this concept is applied to a system for delivering high peak energy ultraviolet laser pulses to thereby enhance the efficiency of the energy transmittance. Preferably, the silica that makes up the fibers contains about 200 to 2000 ppM of the $OH^-$ radical, most preferably 1200 ppM.

In another embodiment of the invention, the silica that is used to produce the fibers of the delivery system is doped with fluorine. Fluorine doped silica exhibits even lower attenuation than high OH silica. It appears that the fluorine functions to shift the absorption band gap in the $SiO_2$ structure, to facilitate the transmittance of a large number of photons at low wavelengths. For multimode fibers having diameters in the range of 100 micrometers to 1500 micrometers, the silica preferably should contain between 0.25 and 2.0 wt % fluorine, most preferably 1.0 wt %.

As a further feature of the invention, the silica can be doped with both the $OH^-$ radical and fluorine. When both f these materials are used in combination, the OH radical content should range between 200 and 2000 ppM, and the fluorine should comprise between 0.5 and 3 wt % of the silica.

In the context of the present invention, the fiber can be a single fiber or a bundle of fibers having a total diameter in the range of 100–2,000 microns. A bundle of close-packed small-diameter fibers is preferred because they provide greater overall flexibility and thereby more easily accommodate the twists and tight turns that are required to feed the delivery system through body cavities. This is particularly desirable where a larger diameter waveguide is required to deliver a relatively large diameter beam, such as in vascular angioplasty. This entire structure can be surrounded by a protective flexible jacket 28 mad of a material which is not damaged by ultraviolet light. More particularly, when the fiber undergoes sharp bends, for example at the juncture of two arteries, light losses occur. These losses may be enough to melt some types of jacket materials such as Silicone and nylon. However, UV light resistant materials, for example UV cured acrylate compound or Teflon ®, can sustain high bending losses without degradation and are therefore more desirable for the jacket.

In a preferred form of the invention, the protective jacket is incorporated as part of the fiber itself, rather than being a separate piece of structure which surrounds all of the fibers. As noted previously, every fiber comprises a core and a cladding which surrounds the core to maintain the transmitted light energy within the core. The cross-sectional area of the fiber might normally have a core/cladding ratio of 80/20 to provide suitable flexibility. Typically, both the core and the cladding are made of glass, with the cladding being appropriately modified (e.g., doped) to provide it with a lower index of refraction. In this conventional structure, the protective jacket comprises a third layer which surrounds the core and cladding.

In accordance with one aspect of the invention, the conventional glass cladding is eliminated and the core of the fiber is directly surrounded by a coating of organic material. One specific preferred material is UV-cured acrylate. It has a lower index of refraction than silica, and thereby functions to maintain the laser energy within the core. It also serves to protect the silica glass, and hence eliminates the need for a third layer.

This reduces the overall size of the fiber and hence enables the net cross-sectional area of the core to be increased for a delivery system having a given outer diameter Further details regarding the composition of preferred coatings can be found in U.S. Pat. No. 4,511,209, the disclosure of which is incorporated herein by reference.

A silica fiber of this construction can typically accommodate input energy up to a level around 30 mJ/mm$^2$ produced by a commercially available Excimer laser. If the density of the energy is increased above this level, the input end of a conventional fiber having a planar, polished surface will be damaged or destroyed if the laser is applied directly to it. Unfortunately, this density level is about the minimum that is required to produce ablation of calcified plaque, thus providing no tolerance range if the intended use of the delivery system is for angioplasty. Accordingly, in order to enable a higher level of energy to be conducted in the fiber, an energy coupler 38 can be provided at the input end of the fiber. In the embodiment illustrated in FIG. 2, this energy coupler comprises a section of fiber that has a larger cross-sectional area than the main portion of the fiber. This larger cross-sectional area gradually tapers to the nominal diameter of the fiber, so as to provide a funnel-shaped input section.

Production of such a shape on the end of the fiber can be accomplished by appropriate design of the die through which the silica is drawn to produce the fiber. By interrupting the drawing of the fiber, a bulbous mass remains at one end of the fiber This mass can be cut and polished to produce the funnelshaped input section.

In operation, the increased area of the funnel-shaped coupler decreases the input energy density for a given level of energy within the fiber. Accordingly, the area of the input end can be appropriately dimensioned to enable a sufficient amount of energy for ablation of tissue to be coupled into the fiber without damaging the input end. Once it has been coupled in, the density of the energy is increased by decreasing the cross-sectional area of the fiber within the tapered section, so that a greater amount of energy can be conducted within the fiber than would be possible without such a device.

Figure 3:
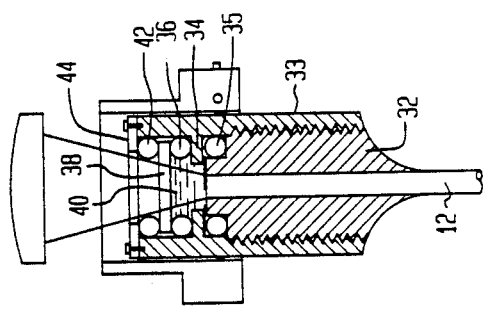
FIG. 3 is a cross-sectional side view of a second embodiment of an energy coupler.

A second embodiment of an energy coupler is illustrated in FIG. 3. In this embodiment, the optical fiber has a uniform diameter along its length and terminates at a flat polished end. The end section of the fiber is encased within a ferrule 32 made of a suitable material such as brass, for example. An aluminum casing 33 having an annular ring 34 projecting from the inner wall thereof is threaded onto the ferrule. A telfon ® O-ring 35 disposed between the end of the annular ring and the ferrule provides a watertight seal between the casing and the ferrule. A second O-ring 36 is disposed on top of the annular ring and supports a glass plate 38 made of z-cut quartz, for example. This arrangement forms a fluid-tight cavity 40 between the ferrule 32, the casing 33 and the glass plate 38. The glass plate can be held in place by means of a third O-ring 42 and a clamping ring 44 disposed on the to of the casing. The fluid tight cavity is filled with liquid which acts as a buffer to the input end of the fiber, enabling laser energy having a relatively high density to be coupled into the fiber without damage thereto. The liquid within the cavity can be distilled and deionized water, or it can be a transparent oil having an index of refraction that is matched to that of the fiber 12, for example.

Figure 4A:
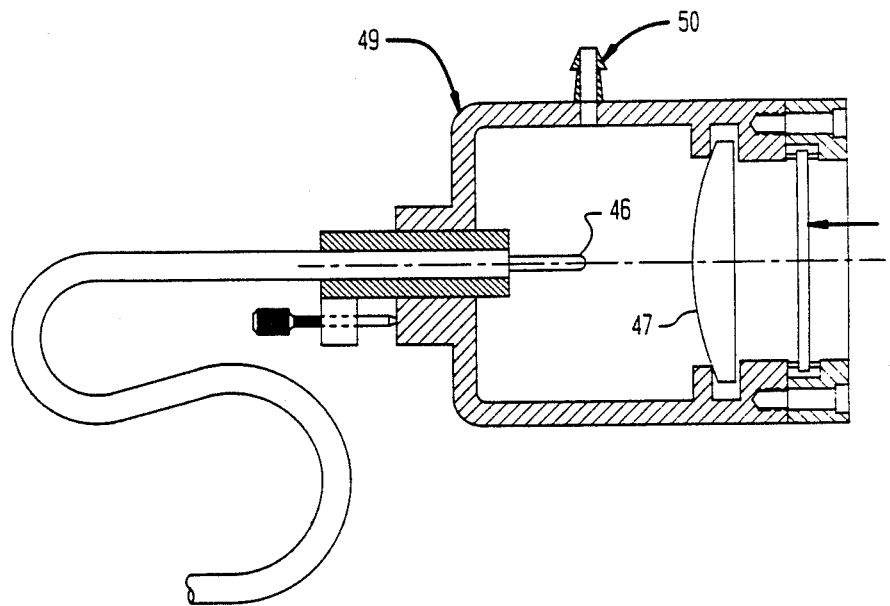
FIG. 4A is a side view, partly in section, of a third embodiment of an energy coupler.
Figure 4B:
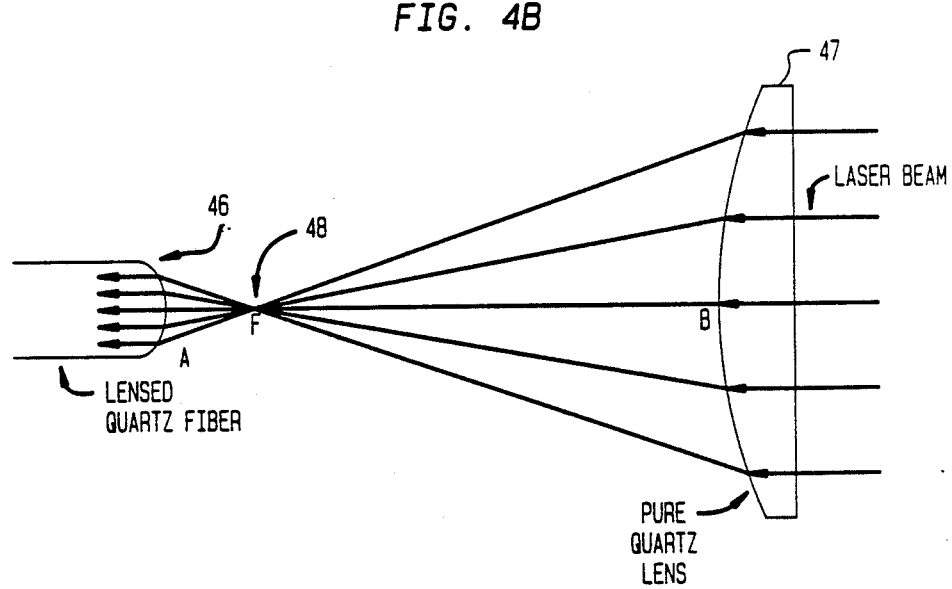
FIG. 4B is an enlarged view of a portion of FIG. 4A, illustrating the principle of operation of this embodiment.

A third, and preferred, embodiment of an energy coupler is illustrated in FIGS. 4A and 4B. In this embodiment, the input end of the fiber is provided with a fused semispherical lens 46. These lens can be formed by melting the material of the fiber itself with a microtorch, to produce a high purity silica lens with no impurities or cracks. Alternatively, the lens 46 can be a separately ground lens that is attached to the flat end of the fiber. The fiber 12 can be tapered as shown in FIG. 2, or it can have a uniform diameter along its length.

A second lens, preferably a plano-convex lens 47, focuses the input beam from the laser to a focal point 48. The input lens 46 on the fiber is axially aligned with the lens 47 and is located at a distance from the lens 47 which is greater than the focal length of that lens. Thus, the focused laser energy appears to be coming from a point source. The lens 66 collimates this focused energy and couples it into the fiber.

The input end of the fiber with the lens 46 and the focusing lens 47 are housed within a chamber 49. This chamber is provided with a vacuum port 50 to enable the chamber to be evacuated of air. If air were present between the lenses 46 and 47, the highly concentrated energy at the focal point 48 might cause a breakdown of nitrogen and oxygen gases that could contaminate the lens 46. In addition, the vacuum environment keeps out dust and other particles which could settle on the lens 46 and act as a heat sink, destroying the roundness of the lens.

Alternatively, this chamber 49 can be filled with a liquid, such as water or oil for example, which matches the index of refraction of the silica fiber. The higher index of refraction of the liquid reduces the dielectric shock when the pulse propagates from the liquid transmission medium to the fiber, relative to that which is experienced when air is the transmission medium.

Although the preferred embodiment employs a curved lens at proximal input end of the fiber, it is possible to couple the energy into a fiber having a planar input surface. However, it is important to ensure that this surface is free of scratches and other imperfections. This can be accomplished by heating the end of the fiber with a micro-torch to cause the fiber material to melt and flow slightly, thereby removing the imperfections caused by polishing.

The type of energy coupler shown in FIG. 4A serves to amplify the energy within the fiber. More particularly, the amplification factor is equal to the ratio of the diameter of the laser beam at the lens 47 to the diameter of the fiber. This ratio is also related to the magnification produced by the two lenses. Referring to FIG. 4B, the dimension FB is the focal length of the lens 47 and the dimension FA is the distance between the lens 47 and the focal point 48. The magnification factor of these two lenses is defined as FB/FA. Since this factor must be equal to the laser energy amplification, the appropriate distance between the lenses 46 and 47, i.e., AB=FB+FA, can be determined from the following relationship:

$$\frac{FB}{FA} = \frac{D_L}{D_F}$$

where $D_L$ is the diameter of the laser beam and $D_F$ is the diameter of the fiber.

Although illustrated as a separate element in the figures, it will be appreciated that the energy couplers could be incorporated into the structure of a laser, to provide an integrated laser and coupling system.

The third main component of the delivery system is a lens 51 that can be provided at the distal end of the fiber. This lens operates to further increase the density of the energy once it emerges from the distal end of the fiber by reducing its cross-section to an area smaller than the fiber itself.

Figure 5A:
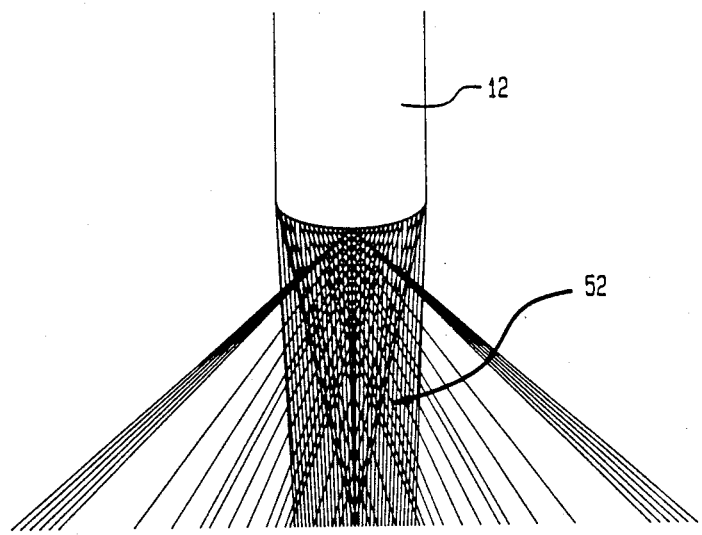
FIGS. 5A and 5B are illustrations of the light pattern which emerges from the distal end of the lensed fiberoptic waveguide.
Figure 5B:
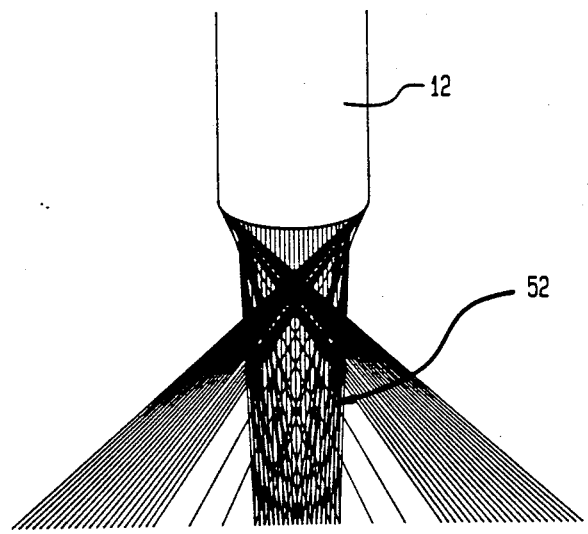

Referring to FIGS. 5A and 5B, two examples of the focused light pattern which emerges from the lens at the end of the optical fiber are shown. As can be seen, a majority of the light emerging from the optical fiber converges upon a focal point or plane 52. Basically, the distance of this focal point from the end of the fiber is determined by the radius of curvature of the lens. In addition, a small amount of the light diverges upon exiting from the optical fiber, so that the resulting light pattern at the focal point consists essentially of an extremely bright spot at the center of the focal point surrounded by a concentric area of lower illumination. As described in greater detail hereinafter, this outer area of lower illumination that is produced by the divergent light rays can be used with advantageous results in an angioplasty system.

Preferably, the lens 51 on the end of the optical fiber is integral with the fiber, i.e. formed from the material of the fiber itself. For example, a micro-torch can be used to melt the flat polished distal end of the tip to a predetermined spherical curvature under a microscope. Alternatively, the lens can be a discrete element separate from the fiber itself and adhered thereto by suitable means which minimizes light reflection at the fiber/lens interface.

Thus, with the combination of the lightly doped synthetic silica fiber, the energy coupler 30 that enables a greater level of energy to be conducted through the fiber and the lens 51 at the distal end which converges the output energy onto a smaller area to thereby increase its density, an amount of high energy laser light that is sufficient to produce an incision can be safely transmitted through an optical fiber waveguide without the risk of damage to the fiber.

To further increase the peak energy that is delivered through the system, it is preferable to slightly increase the length of the pulses beyond the relatively short duration that is typically produced by commercial Excimer lasers and the like. For example, a pulse having a duration in the range of 30–1000 nsec, more preferably 100–300 nsec, enables much higher peak energy to be applied with the same delivery system than a 10 nsec pulse yet is still sufficiently short to produce the desired cutting action. One example of a circuit for stretching the output pulses of a laser is the magnetic switch developed at the Jet Propulsion Laboratory by Drs. J. Ladunslager and T. Tacala.

With the increased energy that is provided by the lengthened pulses, it may not be necessary to provide a lens 51 at the distal end of the fiber 12 to obtain adequate energy density. In fact, the energy level within the fiber might be sufficient to enable the laser beam to be expanded as it exits the fiber, rather than focussed, and still contain sufficient energy density to ablate tissue. By expanding the diameter of the laser beam, for example by means of an increasing taper at the distal end of the fiber, a larger area of tissue is ablated to produce more favorable results towards obtaining better blood flow in a blood vessel while using a small diameter flexible fiber that can be easily propagated through the vessel.

As noted above, one particular application for which the laser delivery system is particularly well suited is the field of angioplasty. In such an application, the optical fiber for the delivery of the laser energy can also be used to deliver the visible light that illuminates the interior of the vessel. While it is desirable to focus the laser energy so as to increase the density level, the opposite effect is normally preferred for the visible light. In other words, it is preferable to illuminate as wide an area as possible in order to give the physician a full view of the blood vessel in the vicinity of the end of the fiber. As shown in FIGS. 5A and 5B, although most of the energy is concentrated a the focal point 52, some of the light rays diverge upon emergence from the fiber. It is possible to make use of this divergent light to perform the illumination function. It has been found that the amount of light which diverges away from the focal point is generally sufficient to provide enough illumination in the blood vessel to enable the physician to adequately observe the ambient area.

Figure 6:
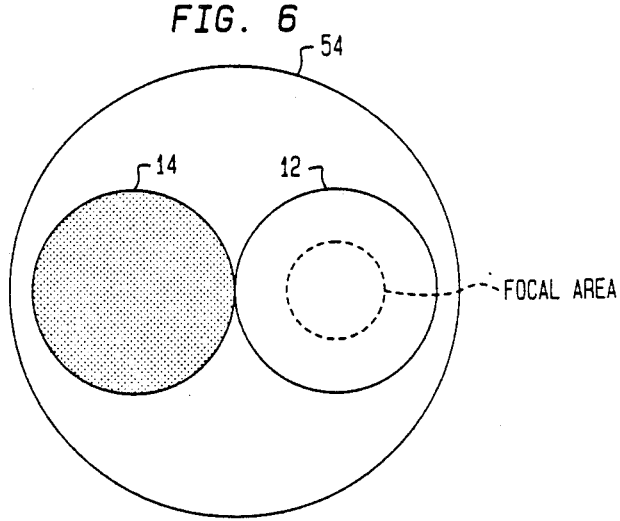
FIG. 6 is a cross-sectional end view of the two fibers that are employed in the laser and image delivery system of the present invention.

Thus, the angioplasty system need only utilize two optical fibers 12 and 14, one to deliver the laser and visible light energy and the other to return the image to a video camera for monitoring. These two fibers can be placed in a side-by-side arrangement, as illustrated in FIG. 6. Preferably, each fiber has a diameter of about 0.5 mm. They can be encased in a catheter 54 which has an outer diameter that is only slightly greater than 1 mm. The extra space present between the inner wall of the catheter and the optical fibers can be used as a flushing channel, thus making possible the use of the system within most coronary arteries.

Preferably, however, this available space is used to supply a saline solution to the distal end of the fiber-optic waveguide. When a lesion is ablated by high peak energy laser light, such as Excimer laser energy, the ablated products can sputter onto the tip of the fiber. These products provide an absorption site which can lead to destruction of the fiber tip. By interposing a continuous layer of saline solution between the tip of the fiber and the lesion, debris is prevented from settling on the fiber tip.

Furthermore, it has been found that a liquid interface provided by a saline solution or blood enhances the ablation process. The liquid does not allow the ablation products to be deposited onto the distal fiber tip. In the case of saline, the solution has an index of refraction which is closer to that of the fiber-optic material than that of air. Accordingly, a smaller shock wave is reflected back into the fiber.

In addition to enhancing the ablation process, the liquid interface of saline displaces the opaque blood and increases the visibility in that region. However, the saline is quickly intermixed with the blood, thus reducing its effectiveness in increasing visibility.

With reference to FIG. 11, an additional preferred embodiment of the present invention includes an inflatable balloon 90 located around the lens output at the distal end 94 of the endoscope 80. The balloon preferably comprises an elastic and transparent material such as latex or polyethelene. At the opposite end of the endoscope 80, an input 88 is provided for pumping saline through a flushing channel 82 along the endoscope 80 into the balloon 90 at the distal end 94. An eyepiece 84 is also provided adjacent the input 88.

In operation, saline is pumped through the input 88 and flushing channel 82 into the balloon 90 under sufficient pressure to inflate the balloon 90. As the balloon inflates, opaque blood, normally surrounding the distal end 94 of the endoscope 80 is displaced by the clear saline and balloon 90, thus providing a region of enhanced visibility before the endoscope 80. Because the saline is retained in the balloon 90, it does not enter the circulatory system, thus reducing risk to the patient.

While advancing the endoscope 80 through a blood vessel, the balloon 90 is preferably only partially inflated with saline. In such a position, the balloon 90 acts as a blunting tip for the endoscope, which reduces trauma to the vessel wall during the advancement of the endoscope 80 through the vessel. Once the endoscope 80 has reached the desired location within the vessel, additional saline is pumped into the balloon 90, further expanding the balloon 90 until it touches the vessel wall. In this mode, visibility of atherosclerotic plaque present on the vessel wall can be viewed with the endoscope 80.

An additional application of the balloon embodiment includes providing a laser generator 96 and an optic fiber 92 for carrying laser energy to the distal end 94 of the endoscope 80. The details of the laser system may vary, but are preferably in accordance with the system described herein. Once the distal end 94 makes contact with a lesion to be ablated, lasing of the lesion takes place through the balloon 90.

As an alternative to a two-fiber system as shown in FIG. 6, separate light waveguides can be used for the laser energy and the visible light to provide a depth of field reference for the physician. More particularly, one of the more difficult tasks in the viewing of a body cavity or blood vessel through an endoscope or an angioscope is the determination of the size and location of a given object in the field of view. An inherent characteristic of the wide-angle lens found in these devices is the fact that it distorts the scene and has no focal point outside the lens. This problem is particularly noticeable when the viewing takes place through a single image guide that is located within a tunnel-like environment, such as a blood vessel that is obstructed by a non-uniform three-dimensional lesion.

Figure 7:
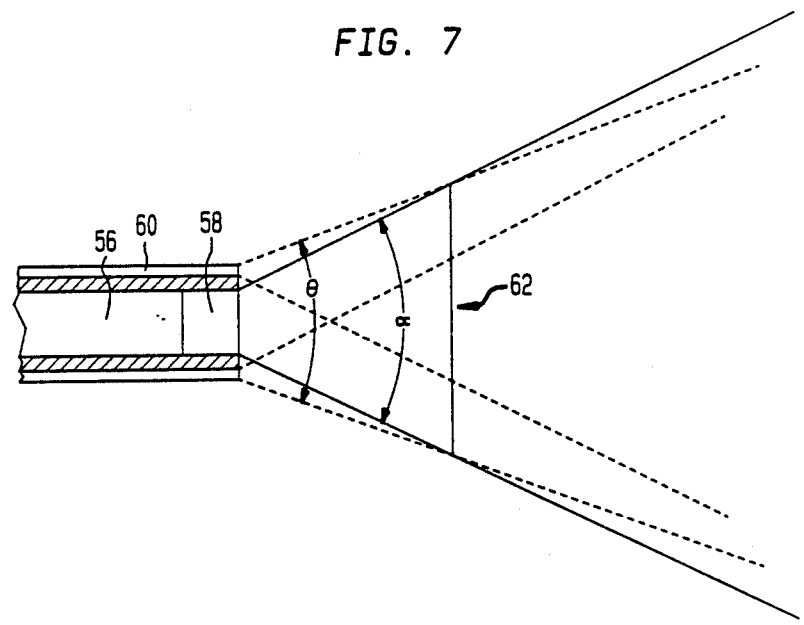
FIG. 7 is a side view of an alternate embodiment of a laser and image delivery system that provides a reference viewing plane within a narrow conduit.

In accordance with another feature of the present invention, however, this drawback can be eliminated by utilizing an illumination beam which has a different divergence angle than the field of view provided by the objective lens on the imaging waveguide. Referring to FIG. 7, the image waveguide 56, which can consist of a single optical fiber or a bundle of fibers, terminates in an objective lens 58 having a field of view which subtends the angle $\alpha$. This image waveguide is surrounded by illuminating light waveguides 60 which project light that diverges over an angle $\theta$. In a conventional endoscope or angioscope, $\theta$ is greater than $\alpha$ so that the entire field of view is illuminated. However, in accordance with one aspect of the present invention, $\theta$ is less than $\alpha$. These angles are determined by the numerical aperture (N.A.) of each of the waveguides 56 and 60, which is in turn related to the index of refraction of the material from which the core and cladding of the waveguide are made. Through appropriate adjustment of these two angles by proper selection of the materials for the waveguides, the illuminating field can be made to intersect the field of view of the lens 58 at a reference plane 62. For example, the N.A. of the image waveguide 56 could be 0.35 and that for the light waveguides 60 can be 0.20 to provide a reference plane that is about 2 mm from the end of the lens 58.

In practice, when an object is viewed through the image waveguide, the light reflected from that object will completely fill the field of view only when it is positioned at the reference plane 62. If the object is farther away from the lens than the reference plane, the illuminated portion of the object will be less than the total field of view, i.e., a dark circle will appear around the object. Alternatively, if the object is closer to the lens than the reference plane, it will appear blurred, followed by an increasing dark area in the center. Thus, the physician can determine the exact location of the distal end of the fiber relative to the viewed object, and hence the size of the object, by adjusting the position of the fiber until the illuminated image completely fills the field of view.

Figure 8:
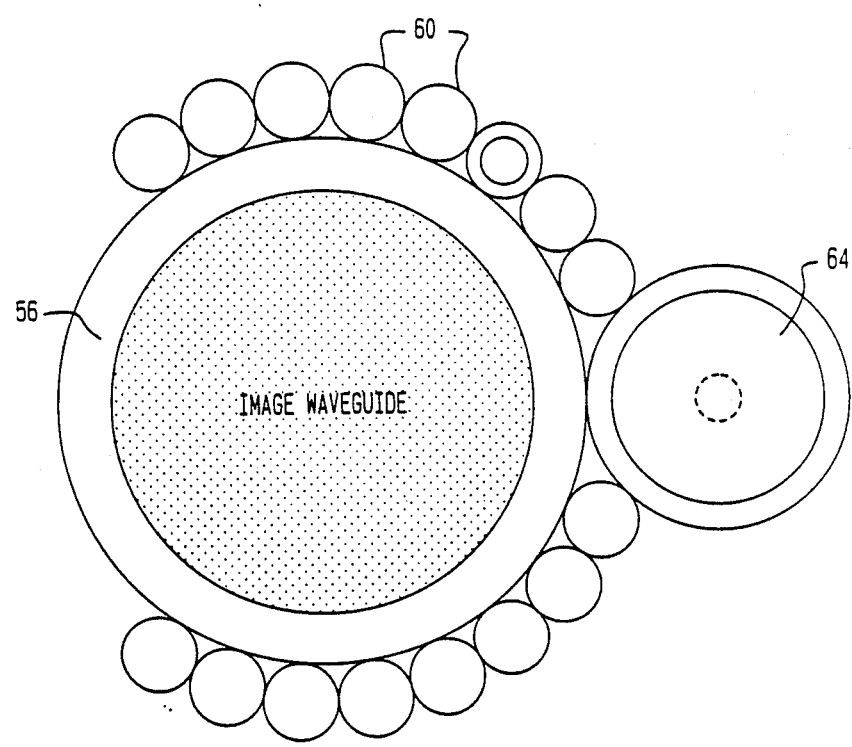
FIG. 8 is an end view of the system of FIG. 7 as incorporated in an angioplasty system.

The incorporation of this principle into an angioplasty system is illustrated in FIG. 8, which comprises the distal end view of the optical fibers. The image waveguide 56 and a lensed laser waveguide 64 are located in a side-by-side arrangement. A plurality of smaller light waveguides 60 are provided around most or all of the remaining circumference of the image waveguide, so that the beam of illuminating light will be concentric with the field of view of the image waveguide. By way of example, the image waveguide can have a diameter of about 1 mm, the laser waveguide can be about 8.5 mm in diameter and the light waveguides can have a diameter between 0.10 and 0.15 mm.

Figure 9:
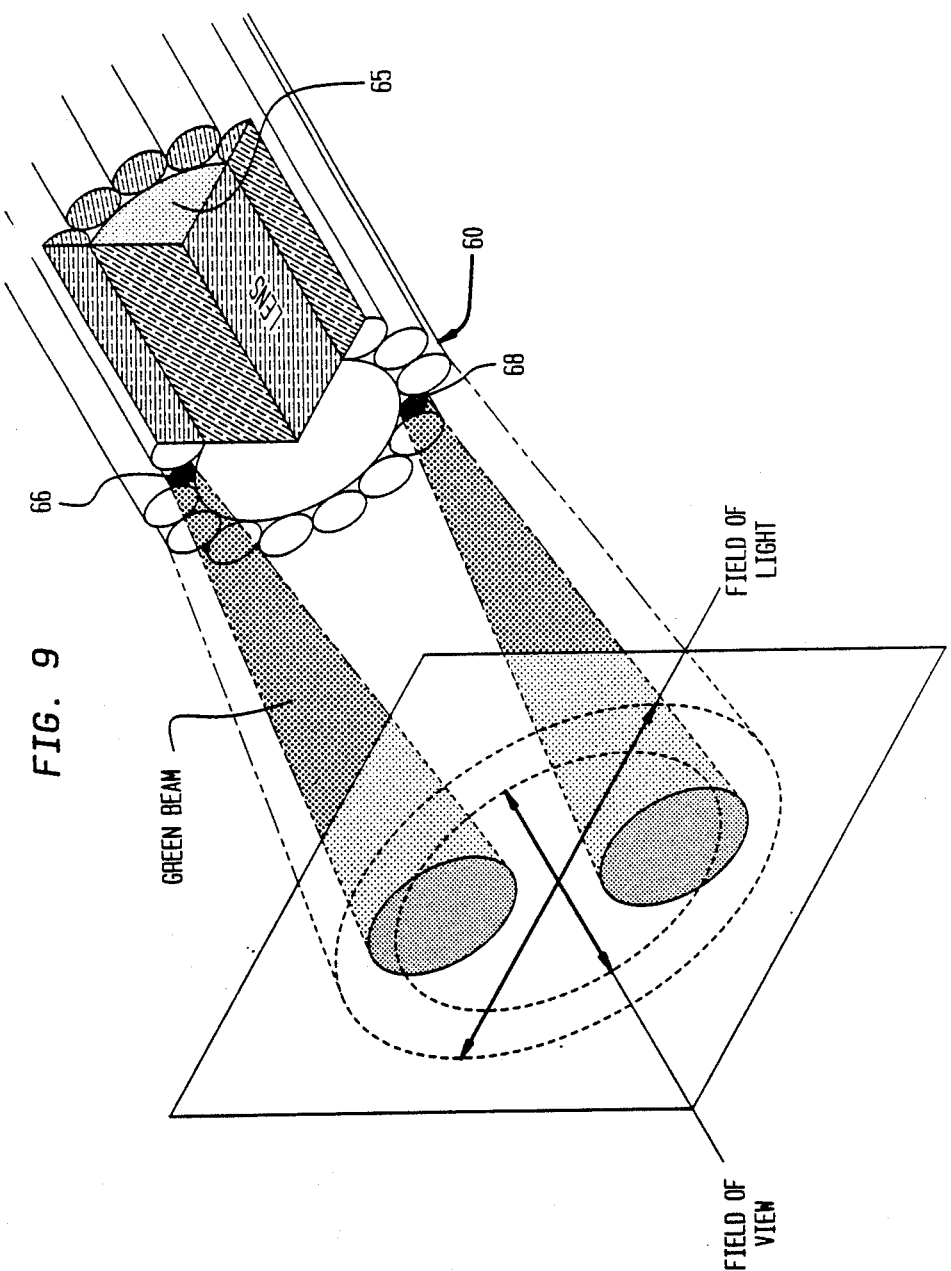
FIG. 9 is a perspective vie of an alternate embodiment for gauging distance and/or size within a blood vessel.

A second embodiment of a measurement system can be implemented using a low-power, colored light beam. Referring to FIG. 9, a beam from a low-power laser or an incandescent light source which produces light in the visible wavelength range, for example a 0.5 mW green laser, is conducted through a dedicated fiber 66 that is separate from the illuminating light fibers 60. The output end of the fiber 66 is cleaved or otherwise appropriately shaped to provide a well-defined divergent beam profile which lies within the field of illumination (shown by the outer dashed line) but partially outside the field of view (inner dashed line).

When the green beam strikes a target such as a lesion, a large green dot will be visible to the viewer. The size of the dot is related to the distance between the tip of the fiber 66 and the lesion. If desired, the reflected image can be provided to a color video camera and a computer-vision system for video information processing to calculate the distance to the lesion, its shape and cross-sectional area, for example by counting the number of pixels subtended by the green dot.

A second green beam light guide 68 can be utilized as shown in FIG. 9. With this arrangement, relative distortion of the two green marker dots can be analyzed to determine the threedimensional profile of the lesion.

While a green laser has been described, it is possible to use any wavelength light whose output beam is visible. However, red laser light in thevvicinity of 630 nm wavelength is not recommended because it is absorbed by human tissue, resulting in a marker dot that is not clearly defined.

While the laser delivery system has been described with the use of a solid core optical fiber comprised of substantially pure synthetic silica when high peak energy ultraviolet light is to be delivered, it is possible to use a hollow-core silica-based fiber for other types of energy having a shorter wavelength than ultraviolet light VUV and XUV. At the distal end of the fiber, the cladding can be melted to produce a spherical lens that concentrates the output beam. This type of lens can be used for light having a wavelength greater than about 175 nm. For shorter wavelength light, a preferred material for the lens is a fluoride glass, such as LiF, MgF or CaF. This lens is a separate element that is appropriately attached to the quartz-cladded hollow fiber.

For infrared laser light, silica has an absorption at about 10 micrometers wavelength, and a hollow silica tube tends to absorb the infrared laser light. To maintain high reflection of infrared radiation in the hollow core fiber, a thin layer of metal, preferably aluminum or gold, is deposited on the inner layer of the tube. The infrared radiation propagates through the interior of the fiber by bouncing along the aluminum layer until it reaches the lens at the distal end.

The metal layer can be deposited using any suitable conventional process. Two preferred techniques are to force a solution containing metallic elements through the tube at high pressure or to pass an organo-metal gas through the hollow core and illuminating the silica walls of the fiber from the exterior to deposit the metal on the interior surface of the wall. The thickness of the resulting metal layer is preferably in the range of about 10 to about 200 angstroms.

Figure 10:
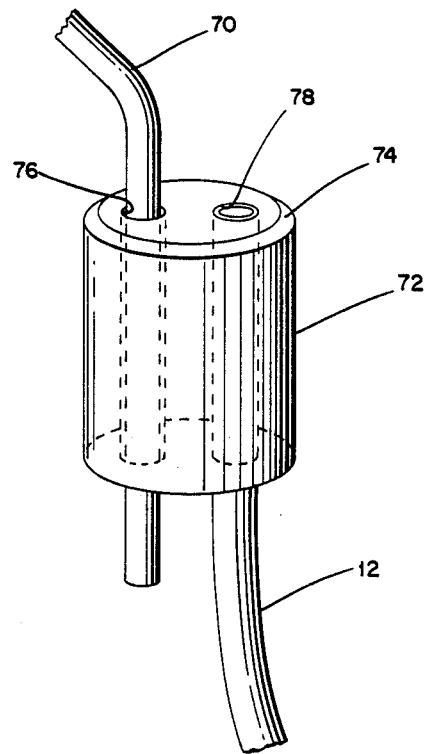
FIG. 10 is a perspective view of a guide wire and sleeve used to control movement of the waveguide.

In order to provide better control of the optical fiber 12, a guidance system may be employed. Referring now to FIG. 10, the guidance system includes a guidewire 70 and a sleeve 72.

The sleeve 72 is preferably between 1 and 200 centimeters in length, and has a rounded tip 74 at its distal end. The tip 74 can be made of stainless steel and glued or welded to the sleeve, or it can be formed integrally on the sleeve 72. The diameter of the tip can vary from 1.2 to 2.5 mm, depending upon the size of the blood vessel. The rounded tip 74 serves as both a dilator to enlarge the blood vessel and as a device to blunt the tip of the optical fiber 12 so as to minimize trauma to the blood vessel.

The sleeve 72 has at least two lumens 76, 78 therein. A first lumen 76 is designed to accept the guidewire 70 and is preferably within the range of twelve-thousandths (0.012) to thirty-eight thousandths (0.038) of an inch in diameter. The diameter of the first lumen may vary, depending on the diameter of the guidewire 70.

The second sleeve lumen 78 is designed to enclose the optical fiber 12, or an array of fibers, if such is the case. The diameter of the second lumen 78 may also vary according to the diameter of the optical fiber 12 or fibers being used. The distal end of the optical fiber 12 is bonded within the second lumen 78 by any suitable means well known to those skilled in the art of bonding.

An array of optical fibers, including an endoscope, as described above, may be used with the sleeve 72 arrangement instead of a single optical fiber 12.

To use the guidance system, the guidewire 70 is threaded through the lumen of the blood vessel by means of an introducer catheter (not shown). The guidewire 70 is inserted up to the location of a total obstruction in the vessel, or in the case of a subtotal lesion, beyond the lesion.

The sleeve 72 is then mounted onto the guidewire 70, with the guidewire extending through the first lumen 76 of the sleeve. The sleeve 72 and the optical fiber 12, which is bound thereto, are then advanced along the guidewire 70 until the sleeve 72 and the distal tip of the optical fiber 12 are adjacent the lesion to be ablated. The combination of the guidewire 70 and the sleeve 72 ensures that the optical fiber 12 remains in alignment with the blood vessel, thus avoiding perforation of the blood vessel by the tip of the optical fiber 12 during positioning of the fiber or by the laser beam during ablation.

Once the fiber 12 is adjacent the lesion, lasing of the lesion is conducted as described above. In a preferred embodiment, the second lumen 78 is eccentrically located within the sleeve 72. In such an arrangement, rotation of the optical fiber 12 while it is in the blood vessel causes rotation of the sleeve 72 which causes the radial position of the optical fiber 12 to shift within the blood vessel. Accordingly, rotating the optical fiber 12 during lasing causes a larger lumen to be ablated within the blood vessel.

Once the lasing is completed, the sleeve 72 and the optical fiber 12 can be withdrawn, leaving the guidewire 70 in place within the blood vessel. Angiographic dye can then be injected through a guiding catheter around the guidewire 70 to evaluate the results of the lasing operation. If the results are unsatisfactory, the entire procedure can be repeated, possibly using different laser parameters or fibers.

It will be appreciated by those of ordinary skill in the art that the present invention can be embodied in other specific forms without departing from the spirit or essential characteristics thereof. The presently disclosed embodiments are therefore considered in all respects to be illustrative and not restrictive. The scope of the invention is indicated by the appended claims rather than the foregoing description, and all changes that come within the meaning and range of equivalents thereof are intended to be embraced therein.

What is claimed is:

1. An angioplasty system, comprising:
   an elongated sleeve adapted to fit within a human blood vessel;
   a guidewire;
   a first means lumen extending axially through said sleeve for guiding said sleeve along said guidewire;
   a fiber optic waveguide; and
   a second lumen extending axially through said sleeve for mounting said fiber optic waveguide to said sleeve; said first and second lumens being parallel and spaced from each other;
   said waveguide and sleeve being adapted to move longitudinally with respect to said guidewire.

2. The system according to claim 1, wherein said second lumen is eccentrically located within said sleeve.

3. The system according to claim 1, wherein said fiber optic waveguide includes an energy-conducting core made of substantially pure synthetic silica and an endoscope.

4. A method of ablating a lesion within a human cavity, comprising:
   inserting a first end of a guidewire into said cavity until the guidewire is adjacent the lesion;
   mounting a fiber-based instrument through a first longitudinal passage in a follower;
   mounting the follower onto the guidewire by passing a second end of the guidewire through a second longitudinal passage in the follower, said second passage being parallel to and spaced from said first passage;
   advancing the follower and fiber-based instrument along the guidewire to the lesion; and
   ablating the lesion with the fiber-based instrument.

5. The method of claim 4, wherein the step of ablating the lesion includes transmitting laser energy through the instrument to the lesion.

6. The method of claim 4, further comprising the step of rotating the instrument within the cavity.

7. The method of claim 4, further comprising the step of withdrawing the instrument and follower after ablating the lesion while retaining the guidewire within the cavity.

8. The method of claim 7, further comprising the step of inspecting the ablation while the guidewire is within the cavity.

9. An angioscope, comprising:
a fiber optic waveguide having a lens output at a distal end thereof;
means for conducting a fluid along the length of the waveguide;
means for supplying the fluid to the conducting means at a proximal end of the waveguide; and
inflatable means for encasing the distal tips of said waveguide and the conducting means in a fluid-tight manner such that fluid supplied to the encasing means by the conducting means under pressure inflates the encasing means and is retained in longitudinal alignment with said waveguide.

10. The angioscope according to claim 9, wherein the inflatable means is substantially transparent.

11. The angioscope according to claim 9, further comprising means for transmitting laser energy through the waveguide.

12. The angioscope according to claim 11, wherein the inflatable means is arranged such that the laser energy transmitted through the waveguide passes through the inflatable means.

13. A system for guiding a fiber-based instrument through a lumen, comprising:
a tubular follower having a first longitudinal passage extending therethrough;
guidewire means extending through said first longitudinal passage and insertable into the lumen for defining a path through the lumen for the fiber-based instrument;
said tubular follower adapted to move longitudinally with respect to said guidewire means through the lumen; and
a second longitudinal passage extending through said tubular follower, said second longitudinal passage being parallel to and spaced from said first longitudinal passage;
said fiber-based instrument being mounted in the second longitudinal passage of the tubular follower.

14. The system according to claim 13, wherein said fiber-based instrument is a fiber optic waveguide.

15. The system according to claim 14, wherein said fiber-based instrument includes an endoscope.

16. The system according to claim 13, wherein said fiber-based instrument includes an energy-conducting core made of substantially pure synthetic silica.

17. The system according to claim 13, wherein said tubular follower is adapted to fit within a human blood vessel.

18. The system according to claim 13, wherein the second longitudinal passage is eccentrically located on the tubular follower.

19. An angioplasty system, comprising:
a source of laser energy;
a fiber optic waveguide receiving said laser energy at a proximal end thereof and delivering said energy to a predetermined site adjacent a distal end thereof, said waveguide having a first diameter throughout a substantial portion of its length;
means at said distal end of said waveguide for expanding the diameter of a beam of laser energy emerging from said distal end to a second diameter larger than said first diameter;
an elongated member adapted to fit within a human blood vessel;
a guidewire;
a first lumen extending axially through said member for guiding said member along said guidewire; and
a second lumen extending axially through said member for supporting said fiber optic waveguide within said member adjacent said distal end of said waveguide.

20. The angioplasty system of claim 19 wherein said source generates pulses of laser energy.

21. The angioplasty system of claim 20 wherein each of said laser pulses has a duration in the range of 100–300 nsec.

22. The angioplasty system of claim 19 wherein said waveguide is comprised of synthetic silica that is substantially free of metallic impurities.

* * * * *